United States Patent
Kotmel et al.

(10) Patent No.: US 6,585,639 B1
(45) Date of Patent: Jul. 1, 2003

(54) SHEATH AND METHOD FOR RECONFIGURING LUNG VIEWING SCOPE

(75) Inventors: Robert Kotmel, Burlingame, CA (US); Hiep Nguyen, Mountain View, CA (US)

(73) Assignee: Pulmonx, Palo Alto, CA (US)

( * ) Notice: Subject to any disclaimer, the term of this patent is extended or adjusted under 35 U.S.C. 154(b) by 18 days.

(21) Appl. No.: 09/699,313

(22) Filed: Oct. 27, 2000

(51) Int. Cl.⁷ .................................................. A61B 1/04
(52) U.S. Cl. ........................ 600/116; 600/114; 600/120
(58) Field of Search .................................. 600/114, 115, 600/116, 120; 264/523, 533

(56) References Cited

U.S. PATENT DOCUMENTS

| | | |
|---|---|---|
| 3,162,190 A | 12/1964 | Del Grizzo |
| 3,866,599 A | 2/1975 | Johnson |
| 3,913,568 A | 10/1975 | Carpenter |
| 4,041,936 A | 8/1977 | Carden |
| 4,086,919 A | 5/1978 | Bullard |
| 4,148,307 A | 4/1979 | Utsugi |
| 4,327,720 A | 5/1982 | Bronson et al. |
| 4,453,545 A | 6/1984 | Inoue |
| 4,690,131 A * | 9/1987 | Lyddy et al. ................ 600/115 |
| 4,716,896 A | 1/1988 | Ackerman |
| 4,784,133 A | 11/1988 | Mackin |
| 4,819,664 A | 4/1989 | Nazati |
| 4,846,153 A | 7/1989 | Berci |
| 4,862,874 A * | 9/1989 | Kellner ........................ 600/116 |
| 4,886,496 A | 12/1989 | Conoscenti et al. |
| 4,913,701 A | 4/1990 | Tower |
| 4,961,738 A | 10/1990 | Mackin |
| 4,976,710 A | 12/1990 | Mackin |
| 5,039,461 A | 8/1991 | Tsushima |
| 5,285,778 A | 2/1994 | Mackin |
| 5,400,771 A | 3/1995 | Pirak et al. |
| 5,478,319 A | 12/1995 | Campbell et al. |
| 5,607,386 A | 3/1997 | Flam |
| 5,645,519 A | 7/1997 | Lee et al. |
| 5,660,175 A | 8/1997 | Dayal |
| 5,762,604 A * | 6/1998 | Kieturakis .................. 600/104 |
| 5,904,648 A | 5/1999 | Arndt et al. |
| 5,954,636 A | 9/1999 | Schwartz et al. |
| 6,258,100 B1 | 7/2001 | Alferness et al. |
| 6,287,290 B1 * | 9/2001 | Perkins et al. .............. 604/509 |

FOREIGN PATENT DOCUMENTS

| | | |
|---|---|---|
| WO | WO 99/01076 | 1/1999 |

\* cited by examiner

*Primary Examiner*—John Rivell
(74) *Attorney, Agent, or Firm*—Townsend and Townsend and Crew LLP

(57) ABSTRACT

Apparatus, methods, and kits, are provided for use in combination with a conventional bronchoscope or other lung viewing scope. In particular, sheaths having an inflatable cuff at their distal end are provided to receive a viewing scope through a lumen thereof. The sheaths thus provide an inflatable cuff on a viewing scope assembly so that the scope can be used in procedures which require selective isolation of regions of a patient's lungs. In particular embodiments, the sheaths may include stop elements for properly positioning a viewing scope therein, pressure transducers for providing accurate lung pressure information during procedures, and the like. Methods for using and forming sheaths having inflatable cuffs are also described.

60 Claims, 13 Drawing Sheets

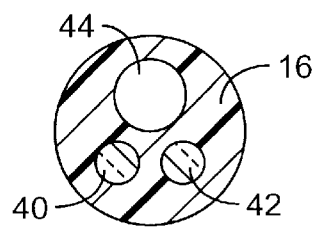
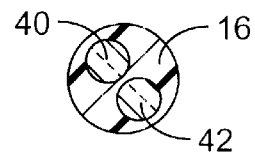
FIG. 2A  FIG. 2B
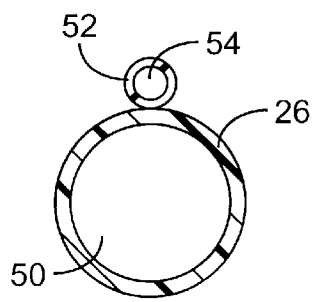
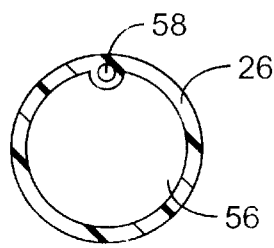
FIG. 3A  FIG. 3B
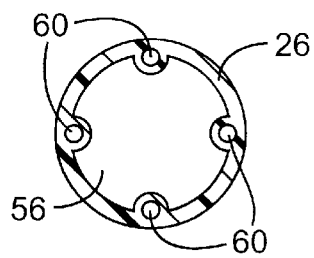
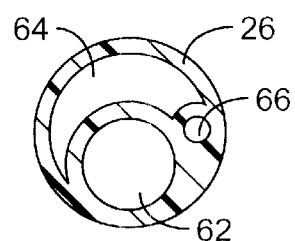
FIG. 3C  FIG. 3D
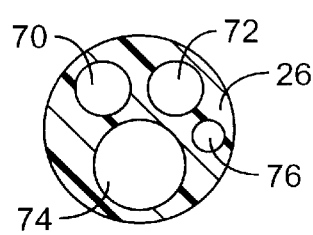
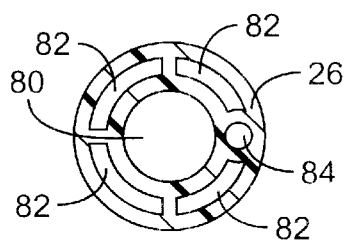
FIG. 3E  FIG. 3F

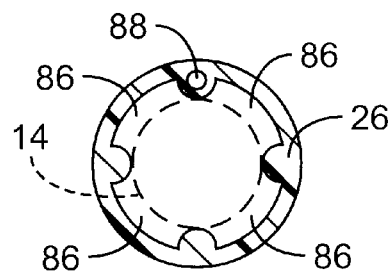
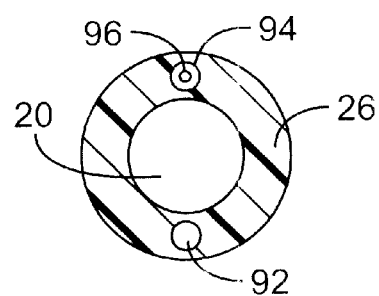
FIG. 3G     FIG. 3H
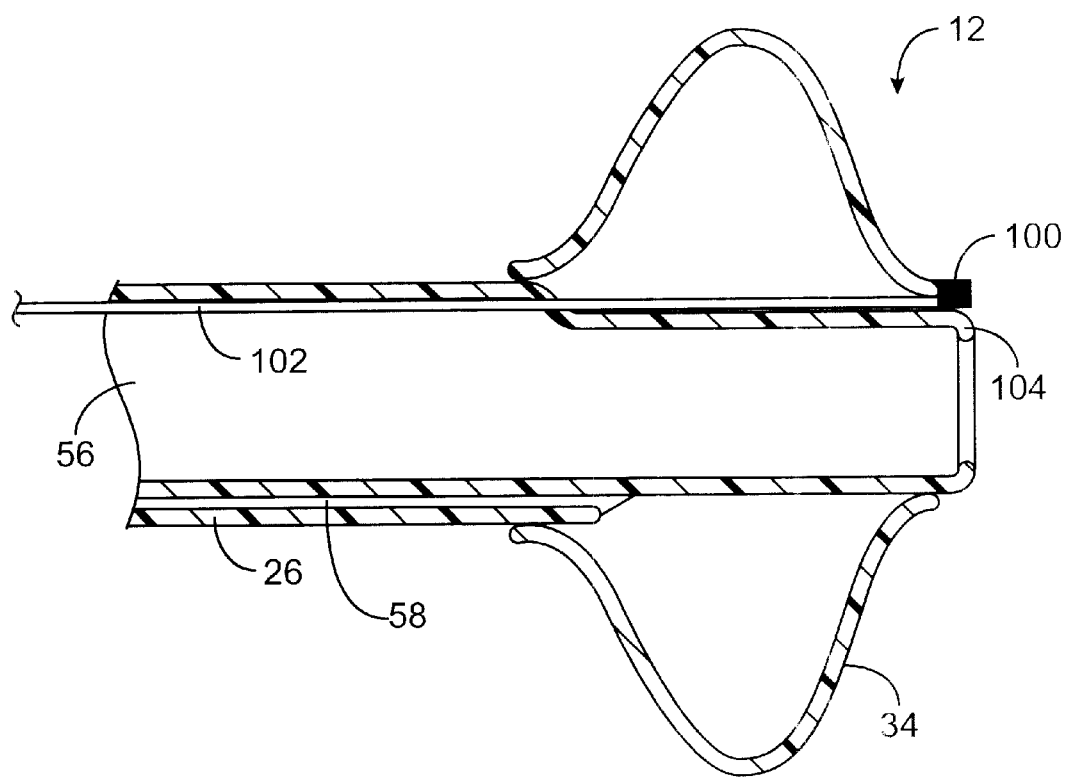
FIG. 5

SHEATH AND METHOD FOR RECONFIGURING LUNG VIEWING SCOPE

CROSS-REFERENCES TO RELATED APPLICATIONS

The disclosure of this application is related to copending appplication Ser. No. 09/699,302, filed on the same day, the full disclosure of which is incorporated herein by reference.

BACKGROUND OF THE INVENTION

1. Field of the Invention

The present invention relates generally to medical apparatus, systems, methods, and kits. More particularly, the present invention relates to methods and apparatus for isolating lobar and sub-lobar segments of the lung and delivering or retrieving substances from such isolated regions.

Lung access and isolation are of interest in numerous therapeutic and diagnostic medical procedures. In particular, access to the lungs is useful for both local and systemic drug delivery, lung lavage, visual assessment and diagnosis of lung function, lung volume reduction, and the like.

For drug delivery, access is most simply achieved by introducing an aerosol to the lungs through the mouth or nose, and a variety of inhalers, nebulizers, metered dose inhalers (MDIs), nasal sprayers, and the like, have been developed over the years. While very effective for many drugs, delivery through the mouth or nose can be very inefficient, often with less than 20% of the drugs reaching circulation or a targeted local treatment region. Moreover, inhalation through the mouth or nose is not able to target drug delivery to a particular region of the lungs. While this may not be a problem for systemic delivery, it can be a significant drawback in the treatment of localized disease where a highly controlled delivery profile would be preferred.

Of more particular interest to the present invention, techniques are presently being developed and implemented for intrabronchial volume reduction ("IBVR") of the lung. Such techniques are described in detail in co-pending application Ser. Nos. 09/347,032; 09/523,061; and 09/606,320. Briefly, IBVR involves introducing a catheter to a lung passageway which feeds a diseased region of the lung. A cuff or other occlusion member on the catheter is then inflated in the lung passageway, and a plug or other obstruction formed in the passageway to occlude the diseased region of the lung. Optionally, the diseased region of the lung may be aspirated and/or drugs or other active substances delivered to that region in order to effect treatment. The IBVR techniques are intended as non-surgical alternatives to lung volume reduction surgery.

Heretofore, it has been proposed to perform both IBVR and lung lavage protocols using an integrated catheter which can be introduced to the lung through the conventional or thin-walled endotracheal tube. In some instances, the procedures are performed without any endotracheal tube with the patient under local anesthesia. The endotracheal tube is positioned in the trachea, and the integrated catheter passed distally through the endotracheal tube and guided to a target site in a lung passageway which feeds the diseased region of the lung. In order to achieve both proper positioning and lung occlusion, the integrated catheter will comprise at least the following components: (1) a viewing scope including both viewing and illumination fibers, (2) a cuff or balloon structure for occlusion of the lung passageway, and (3) a lumen or working channel for delivery of the lung occlusion plug, device, glue, or the like.

Because of the multiple functions required of the integrated catheter, the cost can be significant. In addition to cost, the medical facility where the procedure is to be performed must maintain an inventory of the integrated catheters, which inventory is in addition to all the other lung access, treatment, diagnosis, and other devices which may be routinely maintained by that facility.

One other device which is commonly maintained by medical facilities to perform procedures on the lungs is a "bronchoscope." The bronchoscope is a type of endoscope which is specially adapted to be introduced through an endotracheal tube or directly into a lung passageway to permit viewing of the interior of the lung. The bronchoscope will typically comprise a flexible elongated body, and optical viewing fiber or a video chip, and a light transmitting bundle. The scope may be connected to a conventional viewing system which permits real time viewing of that portion of the lung which has been accessed by the bronchoscope. Optionally, the bronchoscope may include a working channel or lumen to permit conventional procedures, such as biopsy, lavage, retrieval of foreign matter, stent placement, laser therapy, or the like. While the bronchoscopes will typically be formed from a polymeric tube or shaft, it may also be formed from articulated structures which permit introduction through the tortuous regions of the lung. In either case, the bronchoscope will typically not be provided with an occlusion cuff or balloon to permit temporary occlusion of a lung passageway to isolate a region of the lung.

For these reasons, it would be desirable to provide improved apparatus, systems, methods, and kits for accessing and occluding a patient's lungs, particularly a lobar or targeted sub-lobar region of the patient's lungs. The present invention should particularly provide for a modification of a conventional bronchoscope or other lung viewing scope so that the scope can be used in procedures which require selective lung isolation. The modified viewing scopes should be useful for performing a variety of procedures which require both access and selective occlusion, including IBVR, segmental ventilation diagnostics, lung lavage, lung drug delivery, and the like. At least some of these objectives will be met by the invention described hereinafter.

2. Description of the Background Art

U.S. Pat. No. 5,607,386, illustrates a bronchoscope positioned in the lumen of a malleable "stylet" which, in turn, is positioned in a standard endotracheal tube which is cut to 25 cm or less. An endotracheal tube with integral optical viewing and illumination fibers is illustrated in U.S. Pat. No. 5,285,778. A device for treating blebs in lungs and including an elongate member having a balloon and imaging illumination fibers is illustrated in WO099/01076. Other bronchial catheters and treatment systems are described in U.S. Pat. Nos. 5,954,636; 5,904,648; 5,660,175; 5,645,519; 5,400,771; 4,976,710; 4,961,738; 4,886,496; 4,862,874; 4,846,153; 4,819,664; 4,784,133; 4,716,896; 4,453,545; 4,327,720; 4,086,919; 4,041,936; 3,913,568; 3,866,599; and 3,162,190.

The subject matter of the present application is related to that of the following commonly assigned, co-pending applications: U.S. Ser. Nos. 09/606,320; 09/523,016; 09/425,272; and 09/347,032, the full disclosures of which are incorporated herein by reference.

SUMMARY OF THE INVENTION

The present invention provides improved apparatus, systems, methods, and kits for accessing and occluding lung passageways, particularly passageways leading to lobar and sub-lobar regions of a patient's lungs.

The isolated region will be a portion (usually not the whole) of the right or left lung, and isolation will be accomplished by occluding a bronchial passage at least one location in the lobar, segmental, and subsegmental bronchus. Thus, a primary occlusion will be formed after both the main bifurcation of the trachea and a further bifurcation into the lobar bronchus. Optionally, the lobar and/or sub-lobar region can be further isolated at at least one secondary location distal to the primary point of isolation and usually after further branching of the bronchial passages. Isolation at the primary location and optional additional locations within the bronchial passages will usually be effected by expansion of an occlusion member, such as an inflatable cuff, inflatable balloon, or the like.

Once the lobar or sub-lobar region has been isolated, a variety of therapeutic and diagnostic procedures can be performed within the isolated region. A presently preferred therapeutic procedure which can be performed using the systems and methods of the present invention is referred to as "intrabronchial volume reduction" (IBVR). IBVR is a non-surgical technique for isolating and occluding diseased lobar and sub-lobar regions of a patient's lung. A systems and methods of the present invention will provide for access and temporary occlusion of these regions, and the regions may thereafter be permanently occluded and optionally aspirated in order to complete the therapeutic protocol. Such methods are described in detail in co-pending applications Ser. Nos. 09/606,320; 09/523,016; and 09/347,032.

In addition to IBVR therapy, the methods and systems of the present invention are useful for lavage and drug delivery. For example, pharmaceutical formulations including small molecule drugs, biological macromolecular drugs, and the like, can be specifically delivered to the isolated region with minimal or no cross-delivery to other regions of the lungs. Similarly, lavage may be performed within the isolated region with minimal impact on adjacent regions of the lungs. Isolation of the lobar or sub-lobar region permits such drug delivery and lavage procedures to be further controlled by control of the volumes, rates, pressures, temperatures, repetitions, retention times, and other method and system parameters. For example, the pressure within the isolated region can be controlled separately from the pressure or pressures maintained outside of the isolated region. In this way, a variety of delivery parameters can be controlled. By elevating pressure within the isolated region above that in the surrounding regions of the lung, the isolated lobar or sub-lobar region will be expanded which may, in some cases, enhance delivery of a drug or permit more efficient lavage of the region. Alternatively, by elevating pressure within the "other" lung regions above that within the isolated region, the risk of migration of toxic therapeutic or other agents away from the isolated region can be greatly reduced.

In a first particular aspect, the present invention comprises a method for accessing and occluding a lung passageway. The method comprises providing a viewing scope which includes or consists essentially of a flexible elongated body, an optical viewing fiber or video chip, and a light transmitting bundle. The viewing scope may be in the form of conventional bronchoscope or a conventional articulated flexible scope having dimensions suitable for introduction in and through lung passageways to reach the lobar and sub-lobar regions of a patient's lungs. Optionally, the bronchoscope or other viewing scope may include a working channel to permit infusion, aspiration, and/or introduction of other materials, such as adhesives, plugs, and the like, for occluding the lung passageway. Alternatively, a lung occlusion can be achieved through other means. Suitable viewing scopes will have the dimensions set forth in Table II below.

A sheath intended for use with the viewing scope will also be provided. A sheath comprises a flexible tubular body having a proximal end, a distal end, and at least a first lumen therethrough. The sheath will further comprise an inflatable cuff disposed near its distal end, where the inflatable cuff may be inflated through a lumen which is present in the tubular body itself or formed in a separate inflation tube. The viewing scope is introduced into the lumen of the flexible tubular body of the sheath to form an assembly where a viewing end of the viewing scope is located at the distal end of the sheath. The assembly of the viewing scope and sheath may then be introduced to a lung passageway so that the inflatable cuff lies adjacent to a target location in the passageway. The cuff may then be inflated to temporarily occlude the target location.

After such temporary occlusion is achieved, a variety of specific therapeutic, diagnostic, and other procedures may be performed in a region of the lung distal to the temporary occlusion. Of particular interest to the present invention, a plug element may be introduced to the target location in order to permanently occlude the passageway and isolate a lobar or sub-lobar region of the lung. Typically, such introducing comprises advancing the plug element through a lumen of the viewing scope to the target location. Alternatively, introducing may comprise withdrawing the viewing scope from the sheath and advancing the plug element through the lumen of the sheath. Still further alternatively, introducing may comprise advancing the plug element through a second lumen of the sheath while the viewing scope remains in place in the first lumen of the sheath. Of course, more than one introducing step may be employed using any one, two, or three of the alternative introducing techniques just described. In some instances, different plug elements, or different components of a plug element assembly, could be introduced through different lumens, and/or at different times in order to effect the desired occlusion of the lung passageway. Particular plug elements and structures are described in co-pending application Ser. No. 09/699,302, the full disclosure of which is incorporated herein by reference. Similarly, various obstruction devices could be introduced in the same or similar manner to the plug elements. A full description of such devices is provided in co-pending application Ser. No. 09/699,302, assigned to the assignee of the present invention. The present invention will embrace all of these particular approaches.

In a preferred aspect of the method of the present invention, the sheath and the viewing scope may be locked together prior to introducing the assembly to the lung passageway. Such locking may be achieved in a variety of ways, but will usually be accomplished using a Luer or other pneumostatic fitting disposed at the proximal end of the sheath. The fitting may be opened to permit introduction and free axial movement of the viewing scope through the lumen of the sheath. After the viewing end of the viewing scope has been properly aligned with the distal end of the sheath, typically with the distal tip of the viewing scope being located within 1 or 2 mm of the distal opening of the first lumen of the sheath, the fitting may be locked on to the viewing scope.

In a further preferred aspect of the present invention, the viewing scope will be aligned within the sheath by advancing the viewing scope until a distal end of the scope engages a stop element at the distal end of the sheath. The stop element will prevent further distal advancement of the viewing scope and position the viewing end of the viewing scope at the optimal location within the sheath.

In a still further specific aspect of the methods of the present invention, a pressure transducer, such as a solid state pressure transducer bridge or other integrated pressure measurement device, located at or near the distal end of the sheath. A signal representative of the pressure at the distal end of the sheath may be taken out through the sheath using wires, coaxial cable, or other suitable electronic-connecting components. Pressure measurement using a transducer located at the distal end of the sheath is advantageous since it provides a direct measurement in real time. The use of isolated pressure measurement lumens, where the pressure measurement device is located external to the patient, is generally less accurate and suffers from a time delay and signal damping.

The present invention further provides sheaths for use in combination with a viewing scope. The sheath comprises a flexible tubular body having a proximal end, a distal end, and at least a first lumen therethrough. An inflatable cuff is disposed at or near the distal end of the flexible tubular body, and the sheath will have the dimensions set forth in Table I below.

TABLE I

| SHEATH DIMENSION | BROAD RANGE | SPECIFIC RANGE |
| --- | --- | --- |
| Length | 25 cm to 80 cm | 50 cm to 70 cm |
| Inside diameter | 2 mm to 10 mm | 2.5 cm to 6.5 mm |
| Outside diameter | 2.5 mm to 10.5 mm | 3 mm to 7 mm |
| Wall thickness | 0.3 mm to 0.7 mm | 0.4 mm to 0.6 mm |
| Distal cuff spacing | 0 cm to 2 cm | 0 cm to 1 cm |
| Cuff diameter (expanded) | 5 mm to 2 cm | 7 mm to 1.5 cm |
| Cuff length | 5 mm to 5 cm | 7 mm to 2 cm |

In a preferred embodiment, the sheath will further comprise a stop element disposed near the distal end of the tubular body to axially limit the travel of the viewing scope in the first lumen. Typically, the stop element will comprise a barrier which mechanically engages a portion of the viewing scope to prevent further travel by the viewing scope in the distal direction. The stop element may comprise a ring, flange, tube eversion, or the like, and will typically be disposed at the distal tip of the sheath and extend radially inwardly across an outer portion of the first lumen to provide the desired barrier. A wide variety of specific configurations are available. The particular dimensions in geometry of the stop element, however, should be selected so that they will not significantly interfere with either the viewing bundle or illumination bundle provided in the viewing scope.

In a further preferred aspect of the sheath, a distal end of the inflatable cuff will be disposed on the tubular body of the sheath at a distance from the distal end of the tubular body in the range from 0 to 2 cm, preferably 0 to 1 cm, and typically 0.05 mm to 2 cm.

In a further preferred embodiment, the inflatable cuff will be elastic and conform closely to an exterior surface of the tubular body of the sheath when not inflated. The cuff may have a variety of conventional or less conventional geometries, including spherical, cylindrical, disc-like, double disc-like, and the like. The inflatable cuff length will usually be in the ranges set forth above. In a specific aspect of the present invention, the inflatable cuff will be formed as an eversion of the distal end of the tubular body. The everted end of the tubular body will usually be comprised of the same material as the proximal length of the tubular body, optionally being thinned. Alternatively, the distal end of the tubular body can be composed of a different material having different mechanical and/or chemical properties. For example, the proximal portion of the tubular body may be formed from a relatively rigid and/or thicker material, while the distal portion which is everted into the cuff may be formed from a thinner and/or more elastic material.

In other aspects of the sheath, the first lumen may be coated with a lubricious coating, such as hydrophilic polymers (PVP, DMAA, TEGDMA, PVA, PEO, PNVP, etc.), carboxylic acids, cellulose ethers, collagens, and the like. Alternatively, or additionally, the first lumen may be textured to reduce friction, where texturing can include the formation of protrusions along the interior surface, rifling, or other known friction-reducing methods.

The sheath may further comprise a proximal fitting which can be selectively sealed over the viewing scope when the viewing scope is present in the lumen of the tubular body. An inflation lumen of the sheath may be brought out through the fitting or formed in a separate tube which detaches from the tubular body at a point distally of the fitting. The sheath may further comprise a pressure measurement transducer as generally described above in connection with the method.

The present invention still further comprises methods for making a sheath for use in combination with a viewing scope. The methods begin with an unexpanded polymeric tube, typically composed of a nylon (polyamide polymer), a high density polyethylene (HDPE), low density polyethylene (LDPE), a polyurethane, a silicone polymer, a polyester, a polyimide, or the like. The tube may be formed from the same material over its entire length, or optionally a distal portion of the tube (which eventually becomes the inflatable cuff) may be formed from a different material. Preferred cuff materials include silicone polymers, polyethylenes, polyurethanes, flexible vinyl butyrates, polyvinylchloride (PVC), polyvinylidene fluorides, polyolifins, polyesters, polyether/amide block co-polymers, and the like. A ring or other peripheral constraining element is placed over the unexpanded polymeric tube at a preselected distance from a distal end of the tube. The polymeric tube is expanded in a mold which defines an inflation cuff in a portion of the tube distal to the ring, and the ring creates a narrow width location in the expanded tube. The inflation cuff, i.e., portion of the tube distal to the ring, is then everted proximally over the tube, where the ring then defines a distal tip of the everted tube. A proximal portion of the cuff is then sealed to the exterior of the tube (that portion of the tube which then forms the shaft of the sheath) in order to create the inflation cuff. An inflation lumen will be formed in or on the resulting sheath construction. Usually, the unexpanded tube will have at least a second inflation lumen formed in a wall thereof, and the inflation lumen can be opened into the interior of the cuff which is later formed by eversion. Alternatively, a separate inflation tube can be attached to the interior or exterior of the sheath shaft to provide for inflation of the cuff.

The present invention still further provides kits for assembling and using a sheath and viewing scope assembly. The kits comprise a sheath having an inflatable cuff near a distal end thereof and instructions for use setting forth a method for introducing a viewing scope into a lumen of the sheath. The instructions may set forth any of the specific and preferred aspects of the methods of the present invention as described above. Kits will typically further comprise a suitable package for holding the sheath together with the instructions for use. Such packages may comprise any conventional medical device package including boxes, trays, tubes, pouches, or the like. Usually, the sheath will be maintained within the package in a sterile condition.

In all previously described aspects of the present invention, the sheath or sheath structure may optionally be provided with one or more additional inflatable cuffs to facilitate "one lung ventilation." By "one lung ventilation," it is meant that the lung in which the intervention is occurring will be isolated from the other lung, and the other lung will be ventilated. The additional inflatable cuff(s) on the sheath will be used to achieve the lung isolation. Of course, the additional cuff(s) could also be used to isolate lobar or sub-lobar lung segments for other purposes as well.

In a first exemplary embodiment, a sheath will comprise a flexible tubular body having at least a first inflatable cuff disposed near a distal end thereof, generally as described above. A sleeve or equivalent slidable structure will be provided over the exterior of the flexible tubular body, and the sleeve will include at least a second inflatable cuff, usually near a distal end thereof. A second inflatable cuff may be positioned in a lung passageway just distal to the main bifurcation between the two lungs. The second cuff may then be inflated in order to isolate one lung from the other lung. The other lung can then continue to be ventilated, while the procedures of the present invention can be performed in the one lung using the flexible tubular body and first inflatable cuff, generally as described above.

In a second exemplary embodiment, a second and optionally third, fourth, and further additional inflatable cuffs will be disposed directly on the flexible tubular body of the sheath. The first inflatable cuff, which is disposed at or near the distal end of the flexible tubular body will still be positioned at the target lung passageway located within the target lung. One of the second, third, fourth, or further inflatable cuffs will then be selected to isolate the target lung. In particular, that additional inflatable cuff which lies nearest the main lung bifurcation (or other desired isolation point) will then be selectively inflated to provide the desired isolation. The main viewing, biopsy, or other desired procedure may then be performed using the bronchoscope which is introduced through the sheath lumen, generally as described above.

BRIEF DESCRIPTION OF THE DRAWINGS

FIGS. 2A and 2B are alternative cross-sectional views of conventional bronchoscopes which may be used in the methods of the present invention, taken along line 2—2 of FIG. 1.

FIGS. 3A–3H are alternative cross-sectional views of the sheaths of the present invention taken along line 3—3 of FIG. 1.

FIG. 5 is a cross-sectional view of a distal end of the sheath of FIG. 1, shown with a pressure transducer located at its distal tip.

DESCRIPTION OF THE SPECIFIC EMBODIMENTS

The present invention allows the use of conventional viewing scopes, such as bronchoscopes or articulated viewing scopes, in therapeutic and diagnostic methods which require the isolation of a lobar or sub-lobar region of a patient's lungs. Such bronchoscopes and articulated viewing scopes are effective for accessing and viewing lung passageways and distal regions of the lungs. Some bronchoscopes further include a working channel to permit infusion, aspiration, and introduction of therapeutic and other agents. Conventional bronchoscopes and other viewing scopes, however, are incapable of selectively occluding regions of a lung passageway to permit other diagnostic and therapeutic techniques in temporarily isolated portions of the lungs. To that end, the present invention provides a sheath which carries an inflatable cuff which can be used together with a conventional bronchoscope or other articulated viewing scope to permit simultaneous viewing, access, and selective occlusion of a lung passageway.

Figure 1:
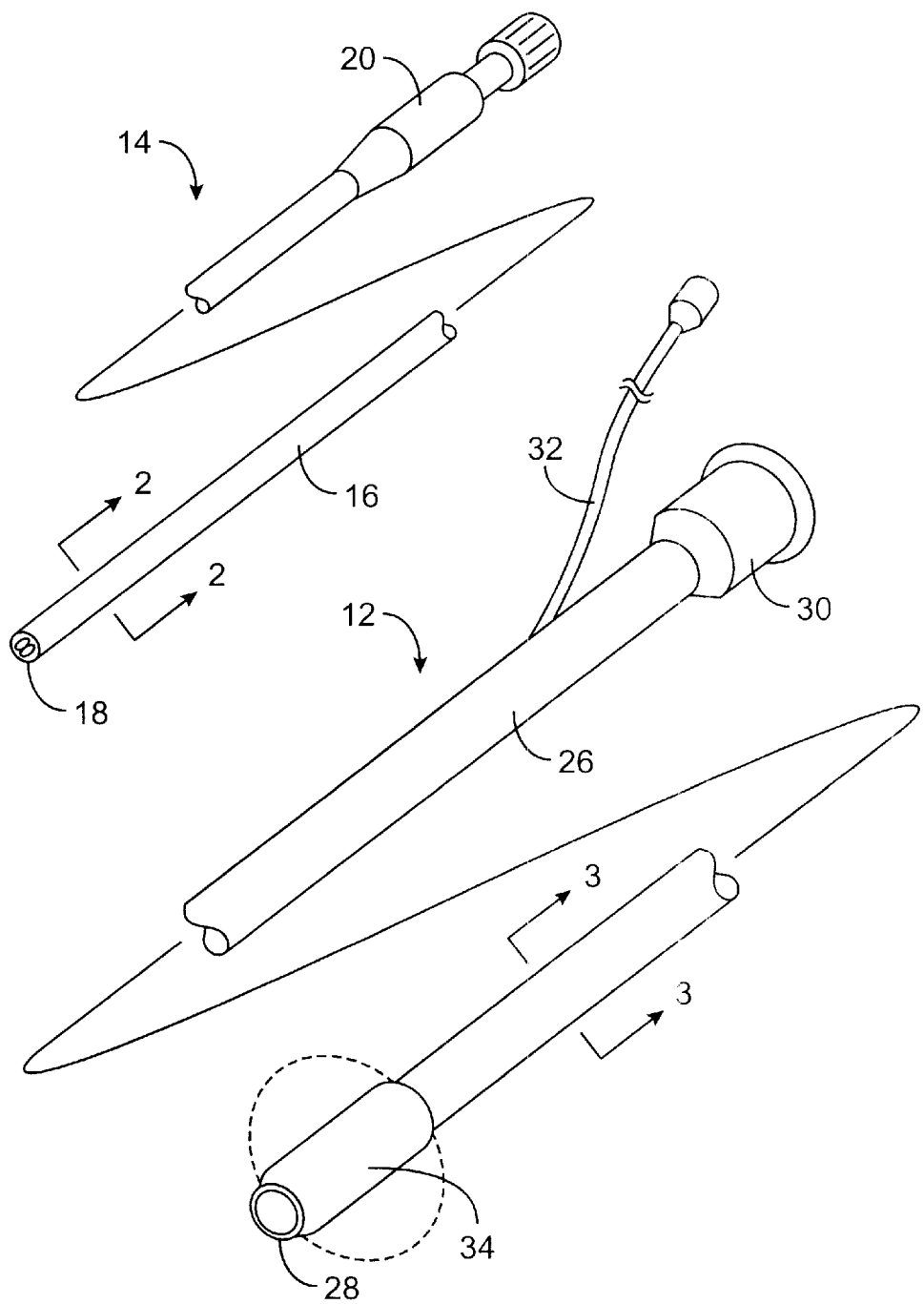
FIG. 1 illustrates a first embodiment of a sheath constructed in accordance with the principles of the present invention in combination with a conventional bronchoscope.

Referring now to FIG. 1, the assembly 10 of the present invention will comprise both a sheath 12 and a viewing scope 14. The viewing scope will typically be a conventional bronchoscope which may or may not include a working channel. Typical dimensions of the bronchoscope are set forth in Table II, as follows.

TABLE II

| VIEW SCOPE DIMENSION | BROAD RANGE | NARROW RANGE |
| --- | --- | --- |
| Length (cm) | 40 to 70 | 50 to 60 |
| Outside diameter (mm) | 1.5 to 8 | 2.2 to 6 |
| Working channel diameter (mm) | 0 to 2.8 | 1.5 to 2.8 |

Conventional bronchoscopes are available from a number of commercial suppliers. Particular bronchoscopes which may be used in the methods and assemblies of the present invention are commercially available from Olympus and Pentax.

Figure 9:
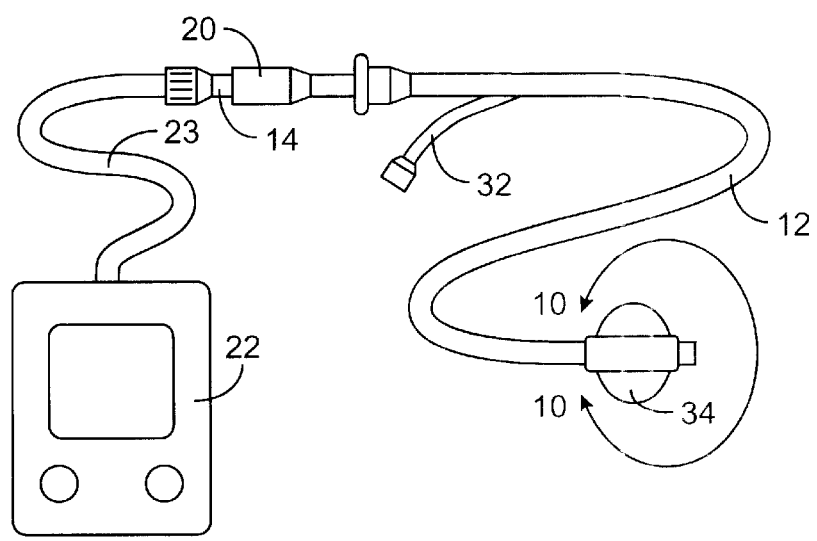

The bronchoscope 14 will comprise a flexible elongated body 16 having a viewing end 18 and a connector 20 which permits attachment to an external viewing scope 22 (FIG. 9).

The sheath 12 includes a flexible tubular body 26 having a distal end 28, a proximal connector 30, and an inflation connector 32. An inflatable cuff 34 is disposed at or near the distal end 28 of the tubular body 26. The inflatable cuff will have the dimensions set forth in Table II above, and may have a variety of specific configurations as described below in connection with FIGS. 4A–4D. Typically, the inflatable cuff will be formed from an elastomeric material which, when uninflated, lies closely over an exterior surface of the distal end of the flexible tubular body 26. Upon inflation, the material of the cuff will simply stretch and permit radial expansion. The elastic nature of the cuff will permit the cuff to conform to irregular geometries of a target lung passageway to provide for effective sealing.

Referring now to FIGS. 2A and 2B, the viewing scope 14 will comprise the elongate flexible body 16 and at least an optical viewing bundle 40 and an illumination bundle 42. Optionally, the viewing scope may further comprise a working channel 44 (FIG. 2A). Alternatively, the viewing scope 14 may be free from a working channel and have a generally smaller diameter, as illustrated in FIG. 2B. Again, specific dimensions are set forth in Table II above.

Referring now to FIGS. 3A–3H, the flexible tubular body 26 of the sheath 12 may have a variety of configurations. Most simply, the flexible tubular shaft will be a simple tube having a single lumen 50. Inflation of the cuff 34 is provided by a separate inflation tube 52 having an isolated inflation lumen 54.

As shown in FIG. 3B, the flexible tubular body includes both a first lumen 56 and a separate inflation lumen 58 formed in a wall thereof.

As shown in FIG. 3C, the flexible tubular body 26 comprises a first lumen 56 and four separate inflation lumens 60 provided in the wall thereof. The four lumens 60 further provide for protrusions which will limit friction as the viewing scope is introduced through the first lumen 56.

Referring now to FIG. 3D, the flexible tubular body 26 may comprise three lumens. The first lumen 62 is intended is intended to receive the viewing scope 14A second lumen 64 provides for a working channel to permit aspiration, infusion, and/or introduction of plug elements as described in more detail below. The third lumen is an inflation lumen 66.

The flexible tubular body 26 of FIG. 3E is similar to that of FIG. 3D, except that a pair of working channels 70 and 72 are provided in addition to the first lumen 74 and the inflation lumen 76.

FIG. 3F illustrates a flexible tubular body 26 having a first lumen 80 and four separate working channels 82 disposed about the first lumen 80. A fifth inflation lumen 84 is also provided.

A flexible tubular body 26 of FIG. 3G is similar to that of 3F, except that the separate working channels 86 are open and closed only when the bronchoscope 14 is in place (as shown in broken line). A separate inflation lumen 88 will also be provided.

FIG. 3H illustrates a flexible tubular body 26 having a first lumen 90 for receiving the bronchoscope, a second inflation lumen 92, and a third lumen 94 which can carry a wire pair or other transmission element for connection of a pressure transducer, as described in more detail below.

Figure 4A:
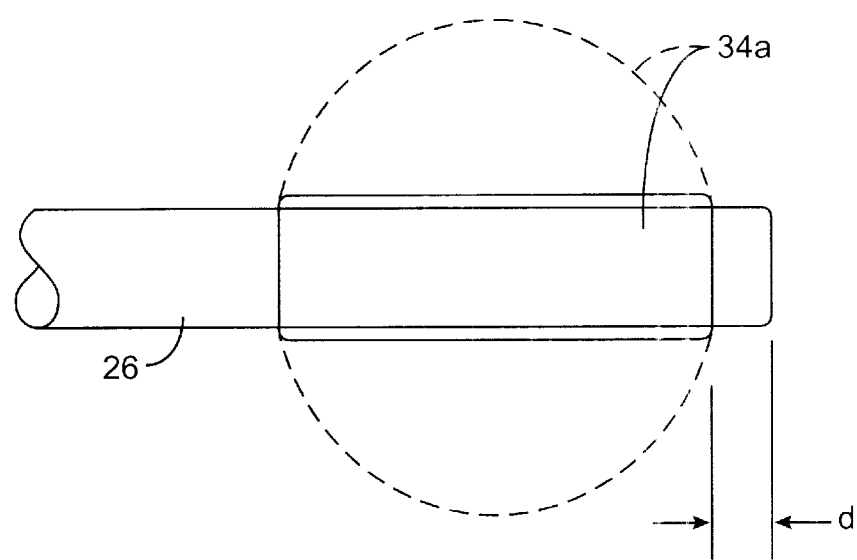
FIGS. 4A–4D illustrate alternative inflatable cuff configurations for use on the sheaths of the present invention.
Figure 4B:
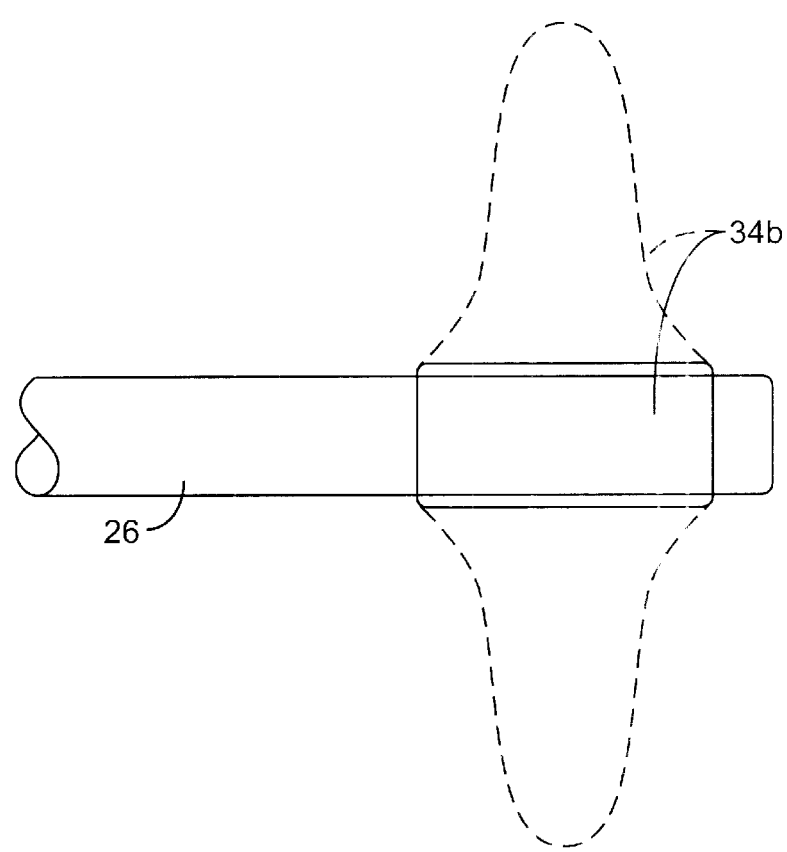
Figure 4C:
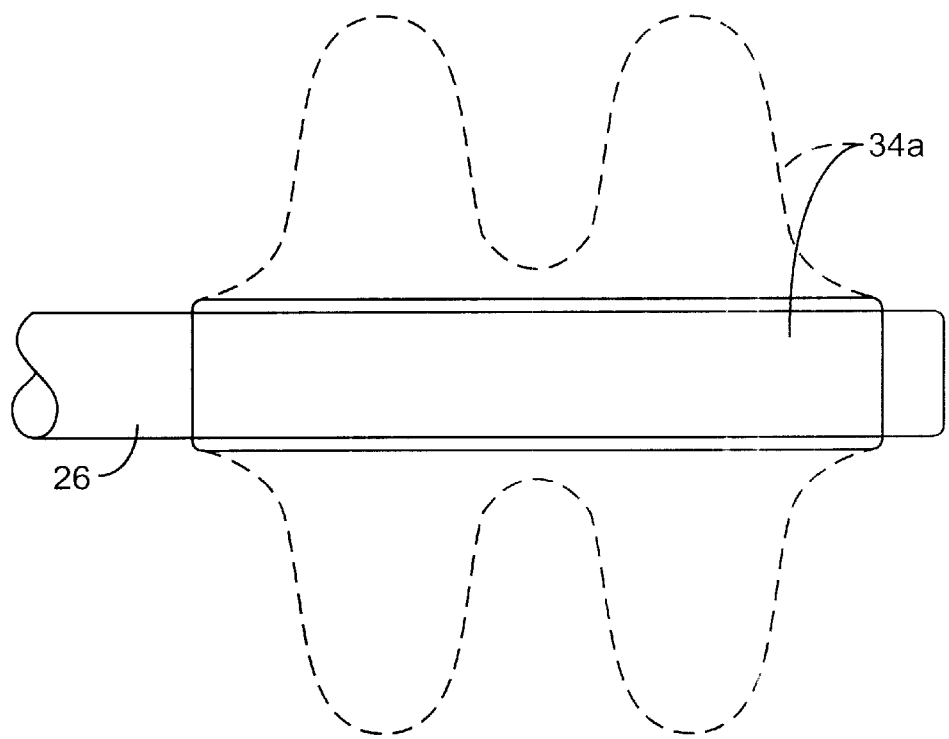
Figure 4D:
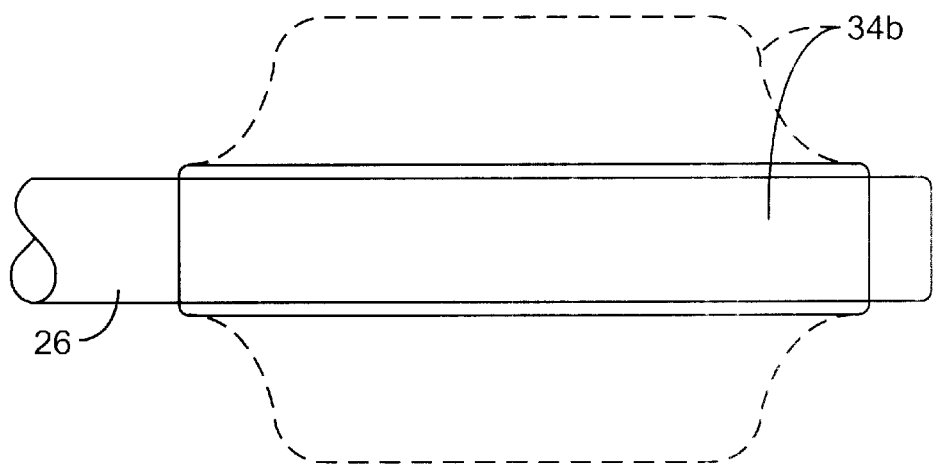

Referring now to FIGS. 4A–4C, the inflatable cuff 34 can have a variety of configurations. In FIG. 4A, an inflatable cuff 34a is shown to have a generally spherical configuration. In FIG. 4B, an inflation cuff 34b is shown to have a generally disc-like configuration. It will be appreciated that the view shown in FIG. 4B is a cross-sectional view taken through the disc. In FIG. 4C, an inflatable cuff 34c is shown to have a double disc-like configuration where a first disc is located near the distal end and a second disc is located proximally at the first disc. Finally, in FIG. 4D, an inflatable cuff 34d is shown to have a cylindrical configuration. In all cuffs, it will be desirable to have a distal end of the cuff be located at or close to the distal tip of the flexible tubular body 26. In particular, as shown in FIG. 4A, a distal end of cuff 34a will preferably be within a distance d from the distal tip of the tubular body in the range from 0 to 2 cm, preferably in the range from 0 to 1 cm.

Referring now to FIG. 5, a representative cross-sectional view of the distal tip of sheath 12 is illustrated. Shaft 26 is shown to have an integral inflation lumen 58, as shown generally in FIG. 3B. An inflatable cuff 34 is shown to have a generally spherical or ovoid configuration, and a pressure transducer 100 is formed at the distal end of the tubular body 26. Pressure transducer 100 is connected to wires 102 or other suitable transmission elements in order to take out an electrical signal representative of the pressure present at the distal end of the shaft. A stop element 104 is formed at the distal tip of the lumen 56. The stop element 104 is shown as a flange which extends radially inwardly from the periphery of the lumen. The stop element 104 will help align the viewing end 18 of viewing scope 14 when it is introduced into the sheath 12.

Figure 6:
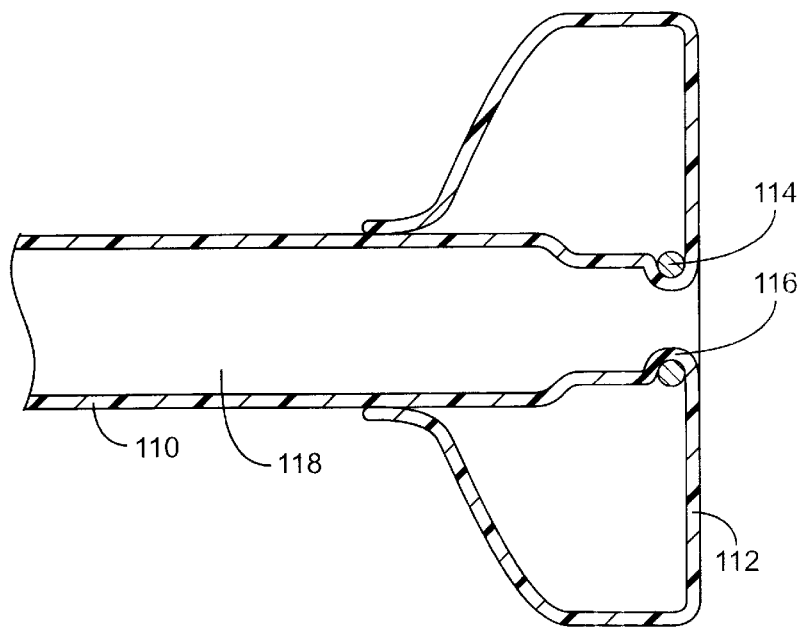
FIG. 6 is a cross-sectional view illustrating an alternative inflative cuff configuration.

An alternative cuff and distal end construction for a sheath 110 is shown in FIG. 6. Cuff 112 is formed integrally with the wall of the sheath 110, as described in more detail below. A retaining ring 114 is present at a distal end of the shaft and defines the stop element 116 which serves to align the viewing scope when introduced through lumen 118 of the sheath. The cuff 112 is positioned at the distal tip of the sheath, i.e., no portion of the sheath or shaft of the sheath extends beyond the distal end of the cuff 112. This is a particularly advantageous construction since it allows the viewing end of the viewing scope to reach as closely as possible to the target location within the lung passageway which is to be viewed.

Figure 7A:
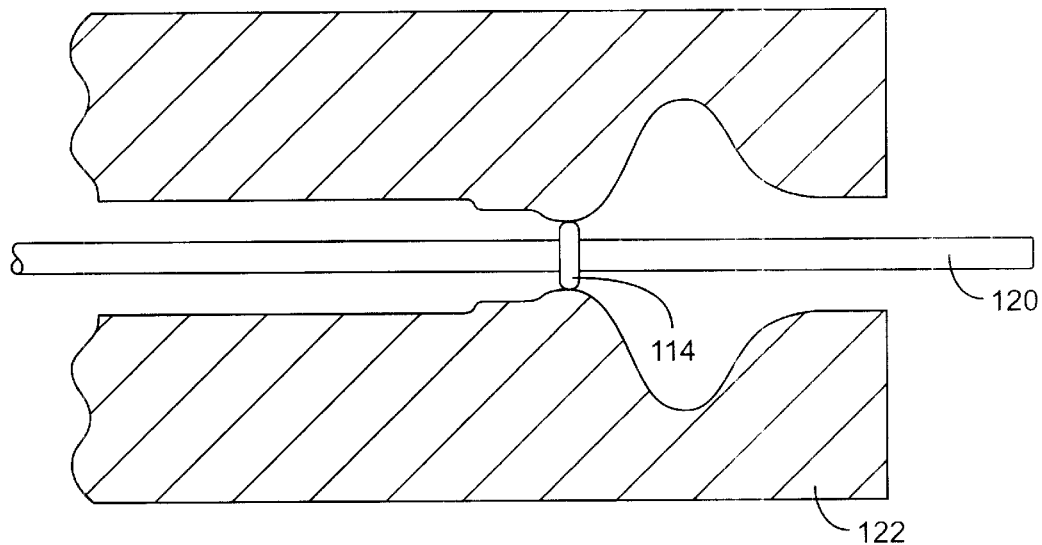
FIGS. 7A–7D illustrate an exemplary cuff construction method according to the principles of the present invention.
Figure 7B:
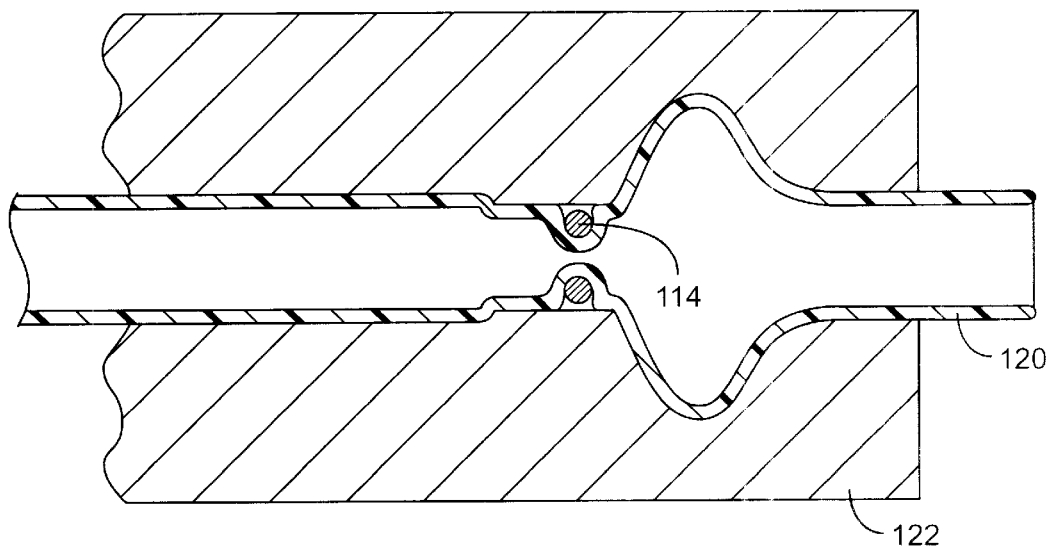
Figure 7C:
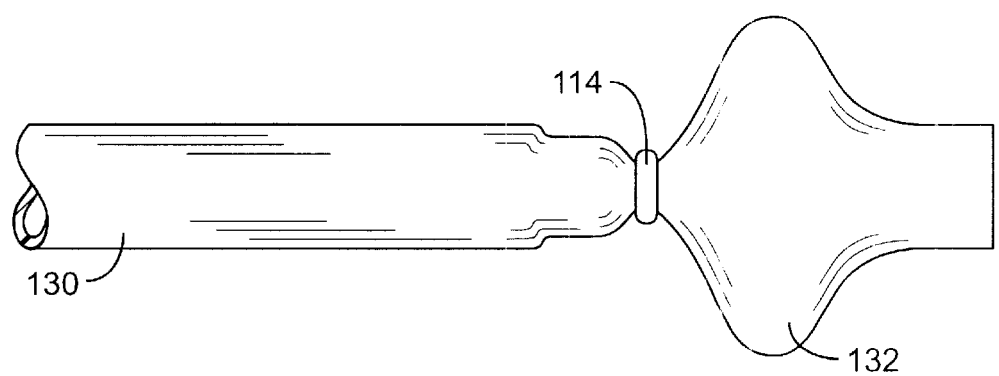
Figure 7D:
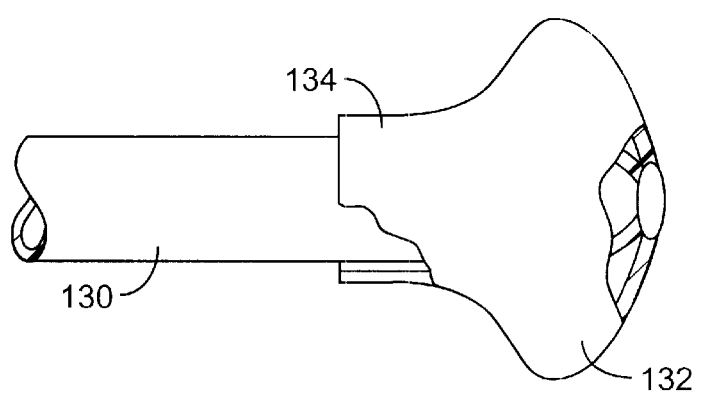

The inflatable cuff assembly of FIG. 6 may be constructed as illustrated in FIG. 7A–7D. An uninflated polymeric tube 120 is placed in a mold 122 with ring element 114 in place over the exterior of the tube. The mold cavity has a particular shape which is imparted into the sheath when the tube 120 is inflated, as shown in FIG. 7B. Inflation is achieved by both heating the tube 120 and applying pressure to the interior of the tube, typically by inflating the tube with air. After the tube has been expanded and cooled, the mold 122 may be removed leaving the structure shown in FIG. 7C. In particular, a proximal or shaft portion 130 is defined together with a cuff portion 132. Cuff portion 132 may then be folded backwardly, i.e., everted, to form the figure shown in FIG. 7D. A now proximal portion 134 of the cuff 132 may be sealed against the exterior of shaft portion 130, typically by gluing, heat welding, ultrasonic welding, or the like. An inflation lumen for the cuff 132 may be formed by adding a separate inflation tube, (not shown) or by relying on an inflation lumen formed within the shaft 130.

Figure 10:
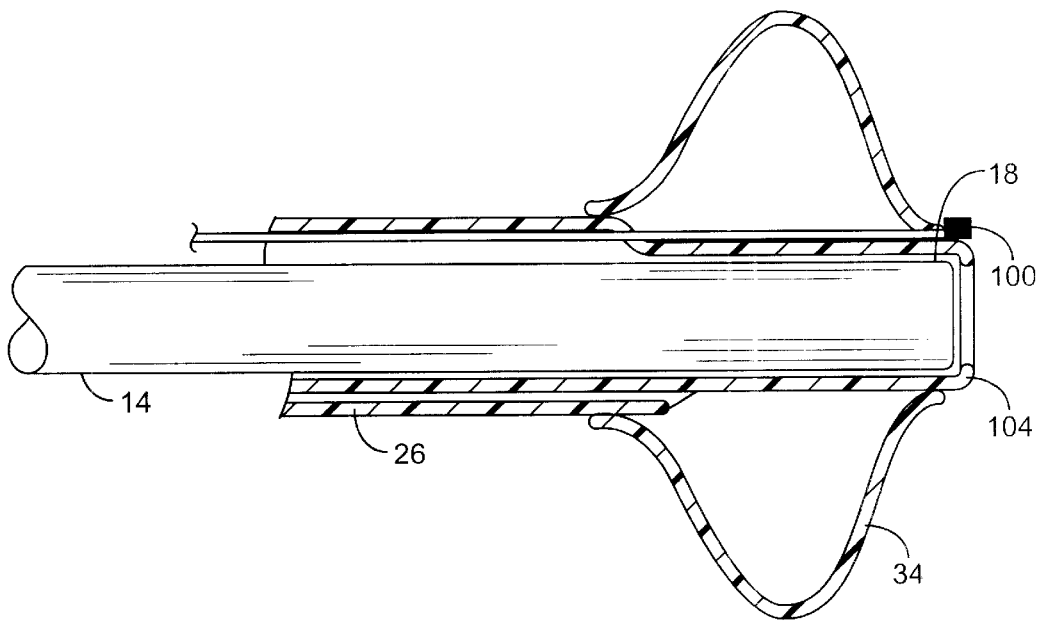
FIGS. 8–10 illustrate methods for assembling a sheath-viewing scope assembly according to the principles of the present invention.
Figure 8:
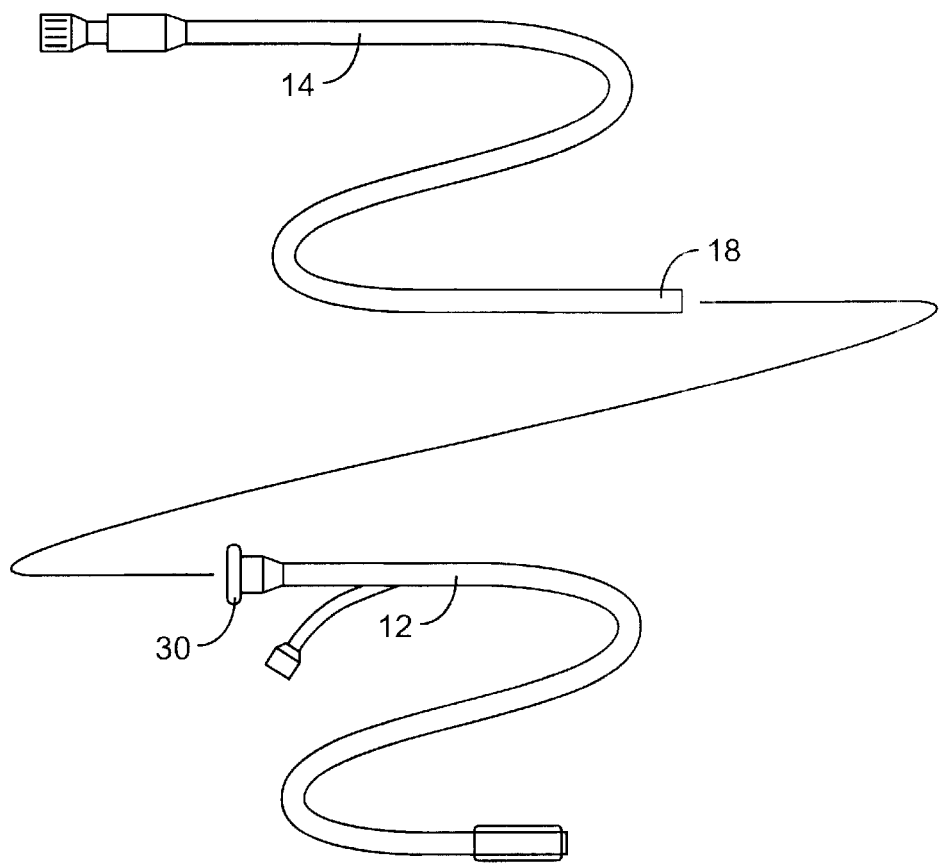

Referring now to FIGS. 8–10, the sheath assembly of the present invention may be formed from a bronchoscope or other viewing scope 14 and the sheath 12 as follows. Initially, the bronchoscope 14 is separate from the sheath 12, as shown in FIG. 8. The viewing end 18 of viewing scope 14 is then introduced through the luer or other proximal connector 30 of the sheath 12. The viewing end is advanced until it reaches the stop element 104, as shown in FIG. 10. At that point, the lower or other connector 30 is then tightened on to the viewing scope 14, as shown in FIG. 9. A suitable monitor 22 may then be connected to the viewing scope 14 in a conventional manner. Inflation of cuff 34 may be effected through the inflation tube 32, typically using a pressurized air or other gas source.

Figure 11:
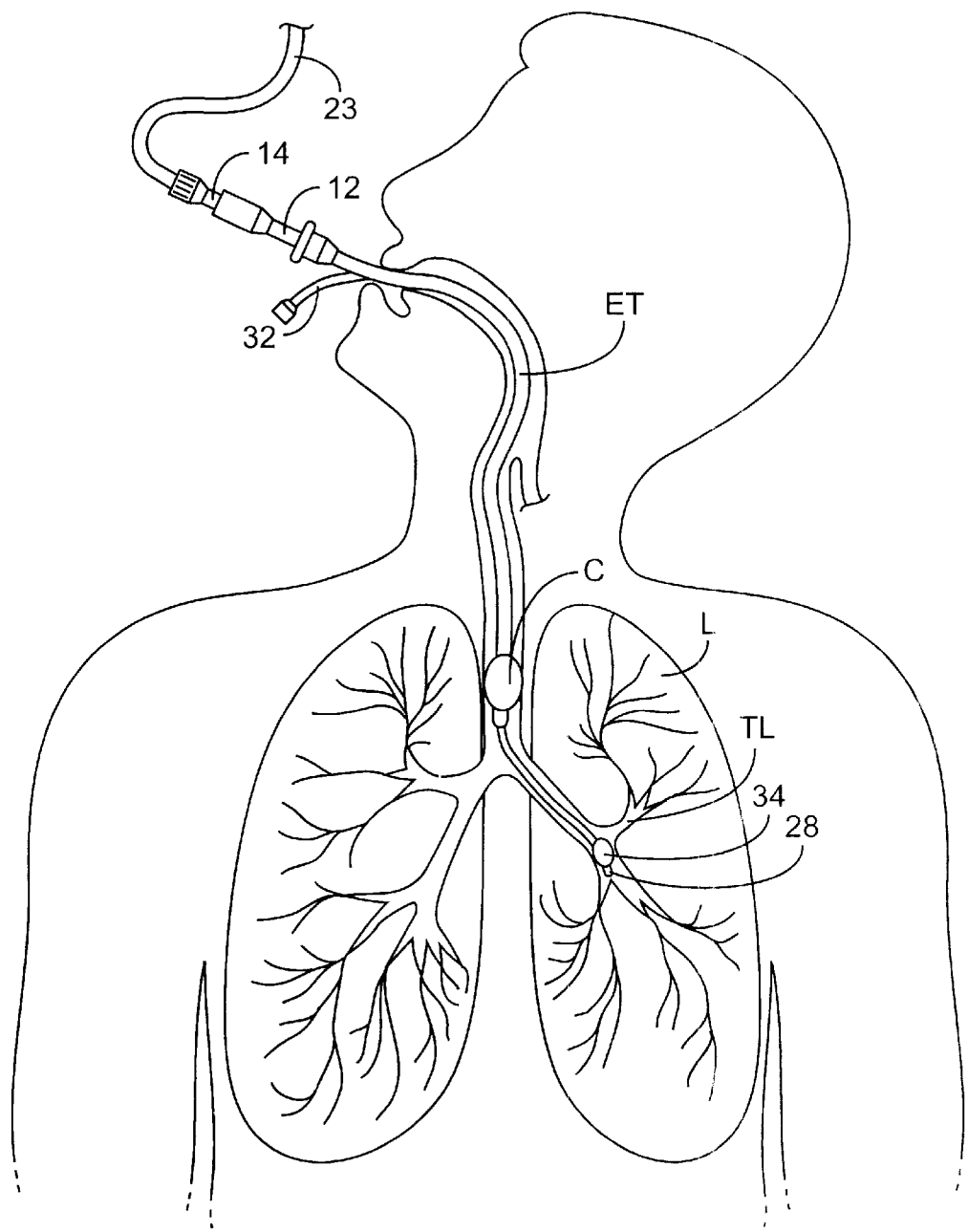
FIG. 11 illustrates use of an assembled sheath-viewing scope assembly in viewing and occluding a region of the patient's lung according to the methods of the present invention.

Referring now to FIG. 11, the assembly of the sheath 12 and viewing scope 14 may be introduced to a target location TL in a patient's lung L. The assembly of sheath 12 and viewing scope 14 will usually be introduced through a conventional endotracheal tube ET which itself has an inflatable cuff C which will typically be located in the trachea immediately above the bifurcation into the lungs. The sheath-viewing scope assembly 12/14 is introduced through the endotracheal tube so that the distal end 28 of the sheath reaches the target location TL. At that point, the inflatable cuff 34 may be inflated through the inflation connector 32. During the advancement and after inflation of the cuff 32, viewing may be accomplished through the monitor 22 which is connected by cable 23. After temporary occlusion has been achieved, as illustrated in FIG. 11, a variety of diagnostic and therapeutic procedures may be performed. In particular, the procedures described in co-pending applications U.S. Ser. Nos. 09/606,320; 09/523, 016; 09/425,272; and 09/347,032, the full disclosures of which have previously been incorporated herein by reference, may be carried out. In the place of plug introduction, the plugs may be introduced directly through a working channel in the viewing scope 14. Alternatively, the viewing scope 14 may be removed from the first lumen of the sheath 12, and the plug (or any other materials), introduced through the first lumen. Still further alternatively, the viewing scope 14 may remain in place, and the plug or other materials introduced through a separate access lumen present in the sheath 12 itself.

Figure 12:
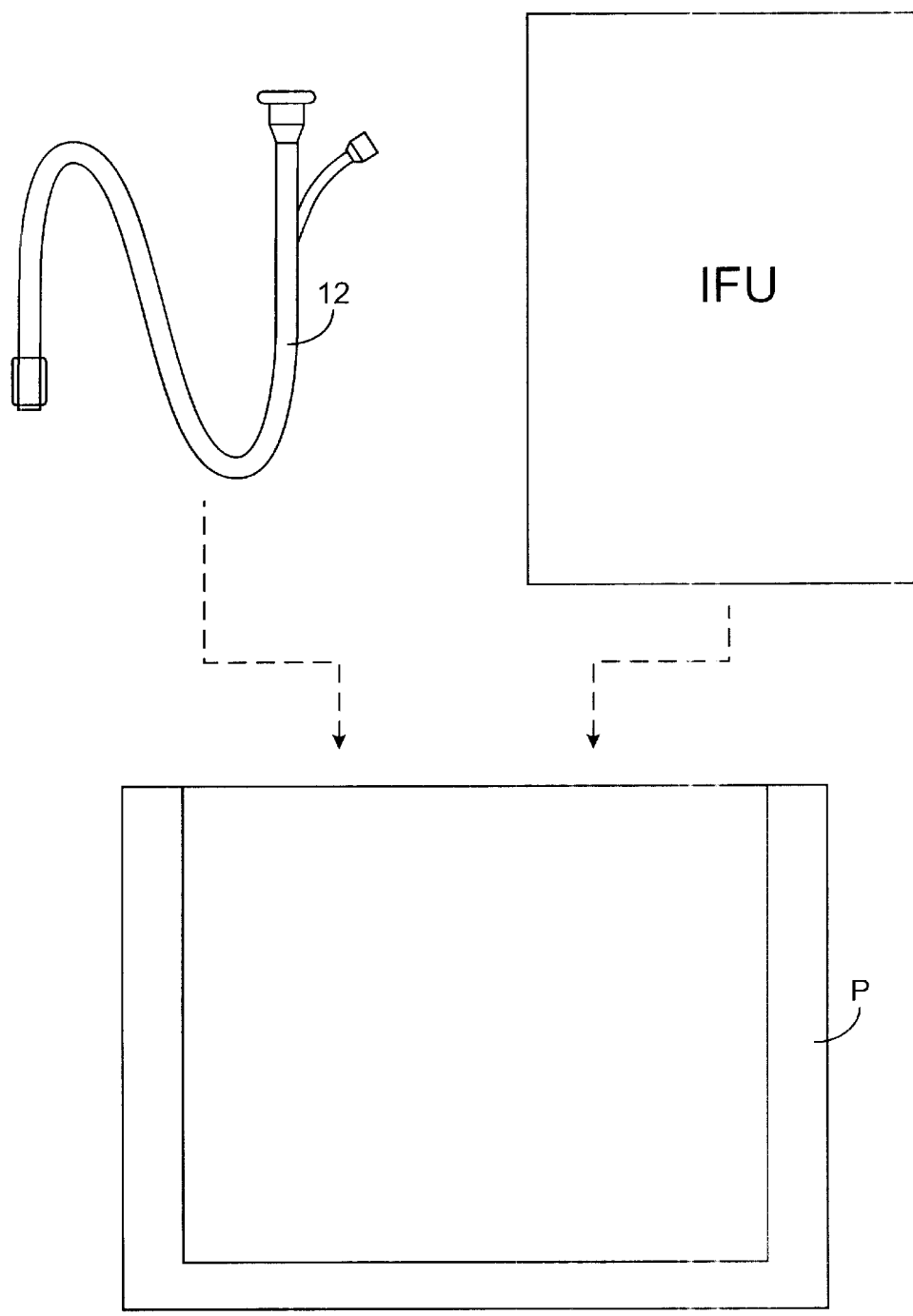
FIG. 12 illustrates a kit constructed in accordance with the principles of the present invention.

Referring now to FIG. 12, kits according to the present invention will comprise a sheath, such as sheath 12 described above, together with instructions for use setting forth any of the methods of use described herein. The instructions for use will typically be printed on an instruction sheet, but could also be provided in electronic form, or printed in whole or in part on packaging. Kits will typically include a package for holding at least the sheath and the instructions for use, such as a conventional box, tray, tube, pouch, or the like. A pouch P is illustrated in FIG. 12. Usually, the sheath 12 will be sterilized and ready for use when placed into the pouch P or other package.

Figure 13:
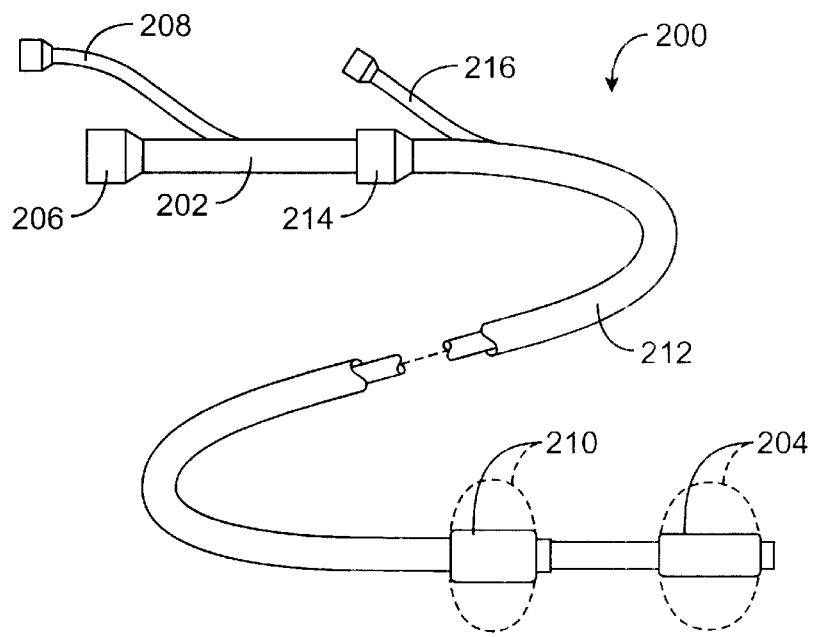
FIG. 13 illustrates an additional exemplary embodiment of a sheath constructed in accordance with the principles of the present invention, which embodiment includes a slidable sleeve structure over a main flexible tubular body portion.

Referring now to FIG. 13, a sheath assembly 200 comprises a flexible tubular body 202 having a first inflatable cuff 204 at a distal end thereof. A Luer or other suitable connector 206 is provided at a proximal end of a flexible tubular body 202, and a separate inflation connector 208 is provided to permit inflation of the cuff 204. As described thus far, the flexible tubular body is generally the same as the sheaths described above, and will include at least one lumen for introducing a bronchoscope therethrough.

Figure 15:
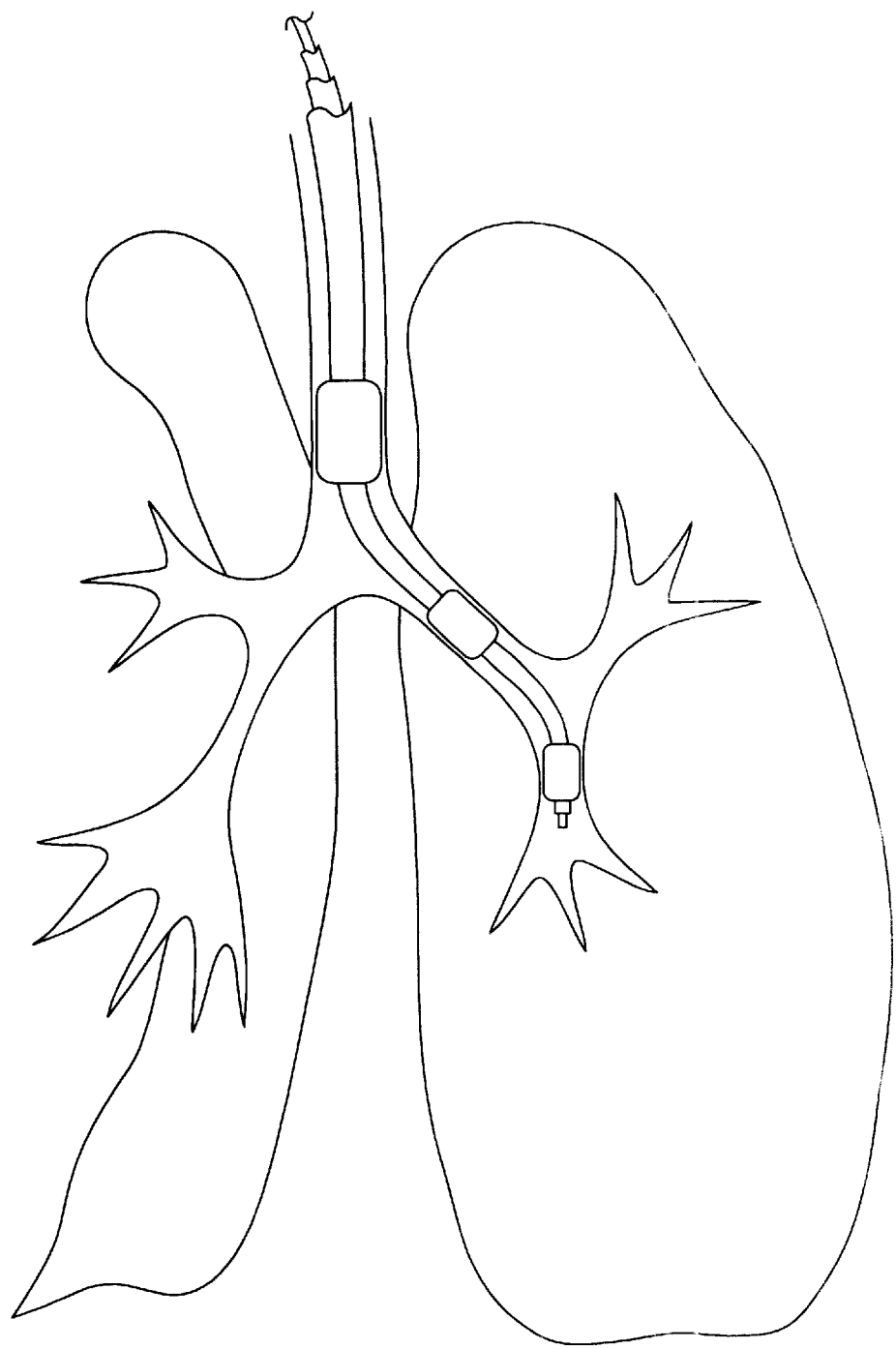
FIG. 15 illustrates use of the sheath embodiment of FIG. 13 in performing a procedure within an isolated lung.

The sheath assembly 200 includes additional structure for positioning a second inflatable cuff 210 at an axially spaced-apart location over the exterior of the flexible tubular body 202. Most simply, the structure may be a sleeve 212 which is slidable mounted over the outside surface of the flexible tubular body 202. In this way, the sleeve 212 can be translated proximally and distally over the flexible tubular body 202 to permit selective positioning of the second inflatable cuff 210. As described in more detail in connection with FIG. 15, the ability to position the first and second inflatable cuffs 204 and 210 relative to one another permits one lung isolation while a selected lobar or sub-lobar portion of lung is further isolated with the first inflatable cuff 204. The sleeve 212 will further include a fitting 214 to permit pneumostatic isolation and a connector 216 to permit selective inflation of the second cuff 210.

Figure 14:
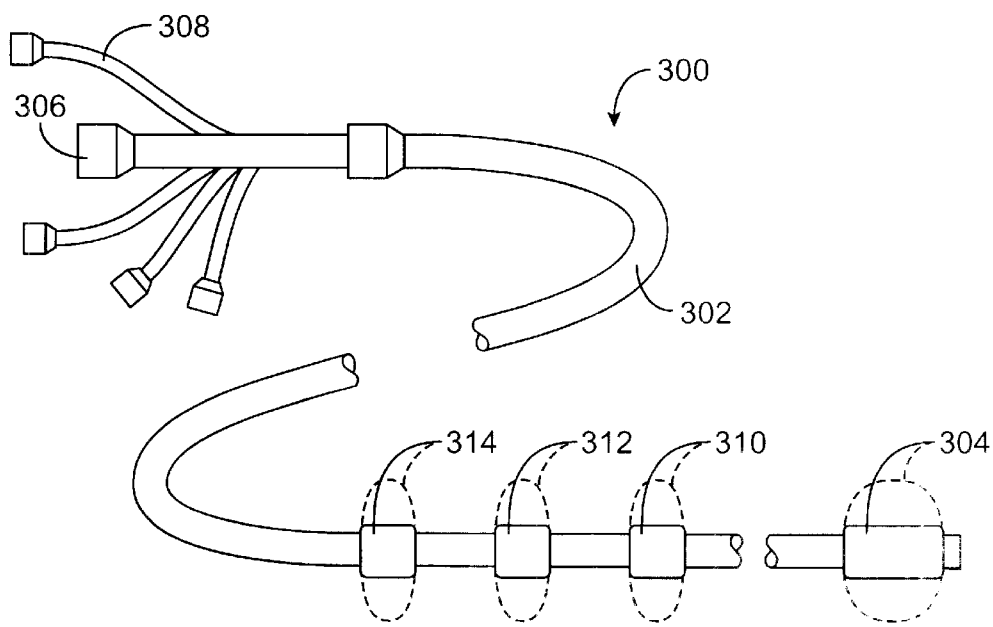
FIG. 14 illustrates yet another exemplary embodiment of a sheath constructed in accordance with the principles of the present invention, wherein the sheath includes multiple inflatable cuffs axially spaced-apart on a flexible tubular body thereof.

A further sheath embodiment 300 is illustrated in FIG. 14. The sheath 300 comprises a flexible tubular body 302 having a first inflatable cuff 304 positioned at or near a distal end thereof. A Luer or other suitable connector 306 is disposed at the proximal end of the flexible tubular body 302, and an inflation connector 308 is provided in order to permit selective inflation of the first inflatable cuff 304

As described thus far, the flexible tubular body 302 is generally the same as the prior embodiments. The sheath 300, however, further comprises at least a second inflatable cuff 310 and optionally a third inflatable cuff 312, a fourth inflatable cuff 314, and further inflatable cuff(s). The additional inflatable cuffs 310, 312, and 314 are axially spaced-apart on the exterior of the flexible tubular body 302. The additional inflatable cuffs are spaced proximally from the first cuff, typically by a distance in the range from 5 cm to 20 cm, and the additional cuffs are spaced from each other by a distance in the range from 1 cm to 10 cm (when more than one additional cuff is provided). The sheath 300 will be used by first positioning the first inflatable cuff 304 at the desired isolation point within a target lung, generally as described with all previous embodiments. At least one of the additional cuffs 310, 312, and/or 314 will then be inflated at a point in a lung passageway proximal to the first isolation point. The second isolation point will be selected to isolate an entire lung or some lobar or sub-lobar region thereof, in order to achieve two levels of isolation. Usually, the entire target lung will be isolated, permitting lung ventilation of the other lung in order to support the patient.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for accessing and occluding a lung passageway, said method comprising:

providing a viewing scope comprising a flexible elongated body, an optical viewing element, and a light transmitting bundle;

providing a sheath comprising a flexible tubular body having a proximal end, a distal end, at least a first lumen therethrough, and at least a first inflatable cuff disposed near the distal end;

introducing the viewing scope into the lumen of the flexible tubular body of the sheath to form an assembly where a viewing end of the viewing scope is located at the distal end of the sheath;

introducing the assembly of the viewing scope and sheath to a lung passageway so that the inflatable cuff lies adjacent to a target location in the passageway;

inflating the cuff to temporarily occlude the target location; and advancing a plug element through a lumen of the view scope to the target location.

2. A method as in claim 1, further comprising locking the sheath to the viewing scope prior to introducing the assembly to the lung passageway.

3. A method as in claim 1, wherein introducing the viewing scope comprises advancing the viewing scope until a distal end of the viewing scope engages a stop element at the distal end of the sheath wherein the stop element prevents further distal advancement of the viewing scope.

4. A method as in claim 1, further comprising measuring pressure in the lung passageway using a transducer disposed on the sheath near the distal end of the sheath.

5. A method as in claim 1, wherein the sheath further comprises at least a second inflatable cuff and the method further comprises positioning the second inflatable cuff in a lung passageway at the entrance to one lung and inflating the second cuff to isolate the one lung and permit ventilation of the other lung.

6. A method as in claim 5, wherein the at least second inflatable cuff is on a sleeve slideable disposed over the sheath to permit separate positioning of the first and second cuffs.

7. A method as in claim 5, wherein the sheath includes at least third and fourth inflatable cuffs spaced-apart from the first and second cuffs and wherein the method further comprises selectively inflating at least one of the second, third, and fourth cuffs to isolate the one lung.

8. A sheath for use in combination with a viewing scope, said sheath comprising:
   a flexible tubular body having a proximal end, a distal end, and a first lumen therethrough; and
   a first inflatable cuff at the distal end of the flexible tubular body;
   wherein the flexible tubular body has a length in the range from 40 cm to 70 cm, an inside lumen diameter in the range from 1.5 mm to 10 mm, a wall thickness in the range from 0.3 mm to 0.7 mm, and the lumen of the flexible tubular body is textured to reduce friction.

9. A sheath as in claim 8, further comprising a stop element disposed near the distal end of the tubular body to axially limit the travel of the viewing scope in the lumen.

10. A sheath as in claim 9, wherein the stop element comprises a barrier which mechanically engages a portion of the viewing scope to prevent further travel by the viewing scope in the distal direction.

11. A sheath as in claim 8, wherein a distal end of the cuff is disposed on the tubular body at a distance from the distal end of the tubular body in the range from 0 to 2 cm.

12. A sheath as in claim 8, wherein the cuff is expandable to a diameter in the range from 5 mm to 2 cm.

13. A sheath as in claim 8, wherein the cuff is elastic and conforms closely to an exterior surface of the tubular body when not inflated.

14. A sheath as in claim 8, wherein the cuff has a peripheral geometry selected from the group consisting of spherical, cylindrical, disc-like, and double disc-like.

15. A sheath as in claim 8, wherein the cuff has a length in the range from 5 mm to 3 cm.

16. A sheath as in claim 8, wherein the cuff is formed as an eversion at the distal end of the tubular body.

17. A sheath as in claim 8, wherein the lumen of the flexible tubular body is coated with a lubricous coating.

18. A sheath as in claim 8, wherein the lumen is textured with protrusions.

19. A sheath as in claim 8, further comprising a proximal fitting which can be selectively sealed over the viewing scope when the viewing scope is present in the lumen of the tubular body.

20. A sheath as in claim 8, wherein the inflatable cuff is connected to an inflation lumen formed within the flexible tubular body to permit inflation thereof.

21. A sheath as in claim 8, wherein the inflatable cuff is connected to an inflation tube which is disposed externally to the flexible tubular body to permit inflation of the cuff.

22. A sheath as in claim 8, further comprising means on the flexible tubular body for measuring pressure near the distal end of the flexible tubular body.

23. A sheath as in claim 22, wherein the means comprises a pressure transducer disposed at the distal end of the tubular body.

24. A sheath as in claim 8, further comprising at least a second inflatable cuff spaced-apart axially from the first inflatable cuff.

25. A sheath as in claim 24, further comprising a sleeve slidable mounted over the flexible tubular body, wherein the second inflatable cuff is mounted on the sleeve.

26. A sheath as in claim 19, further comprising at least a third and a fourth inflatable cuff, wherein said second, third, and fourth inflatable cuffs are disposed directly on the flexible tubular body.

27. A method for accessing and occluding a lung passageway, said method comprising:
   providing a viewing scope comprising a flexible elongated body, an optical viewing element, and a light transmitting bundle;
   providing a sheath comprising a flexible tubular body having a proximal end, a distal end, at least a first lumen therethrough, and at least a first inflatable cuff disposed near the distal end;
   introducing the viewing scope into the lumen of the flexible tubular body of the sheath to form an assembly where a viewing end of the viewing scope is located at the distal end of the sheath;
   introducing the assembly of the viewing scope and sheath to a lung passageway so that the inflatable cuff lies adjacent to a target location in the passageway;
   inflating the cuff to temporarily occlude the target location;
   withdrawing the viewing scope from the sheath; and
   advancing a plug element through the first lumen of the sheath to the target location.

28. A method as in claim 27, further comprising locking the sheath to the viewing scope prior to introducing the assembly to the lung passageway.

29. A method as in claim 27, wherein introducing the viewing scope comprises advancing the viewing scope until a distal end of the viewing scope engages a stop element at the distal end of the sheath wherein the stop element prevents further distal advancement of the viewing scope.

30. A method as in claim 27, further comprising measuring pressure in the lung passageway using a transducer disposed on the sheath near the distal end of the sheath.

31. A method as in claim 27, wherein the sheath further comprises at least a second inflatable cuff and the method further comprises positioning the second inflatable cuff in a lung passageway at the entrance to one lung and inflating the second cuff to isolate the one lung and permit ventilation of the other lung.

32. A method as in claim 31, wherein the at least second inflatable cuff is on a sleeve slideable disposed over the sheath to permit separate positioning of the first and second cuffs.

33. A method as in claim 32, wherein the sheath includes at least third and fourth inflatable cuffs spaced-apart from the first and second cuffs and wherein the method further comprises selectively inflating at least one of the second, third, and fourth cuffs to isolate the one lung.

34. A method for accessing and occluding a lung passageway, said method comprising:
   providing a viewing scope comprising a flexible elongated body, an optical viewing element, and a light transmitting bundle;
   providing a sheath comprising a flexible tubular body having a proximal end, a distal end, at least a first lumen therethrough, at least a first inflatable cuff disposed near the distal end of the tubular body, and a sleeve slidably disposed over the flexible tubular body and having at least a second inflatable cuff thereon;
   introducing the viewing scope into the lumen of the flexible tubular body of the sheath to form an assembly where a viewing end of the viewing scope is located at the distal end of the sheath;

introducing the assembly of the viewing scope and sheath to a lung passageway in one lung so that the first inflatable cuff lies adjacent to a target location in the passageway and positioning the sleeve so that the second inflatable cuff is in a lung passageway at the entrance to the one lung;

inflating the second cuff to isolate the one lung and permit ventilation of the other lung; and inflating the first cuff to temporarily occlude the target location.

35. A method as in claim 34, further comprising introducing a plug element to the target location.

36. A method as in claim 35, wherein introducing comprises advancing the plug element through a lumen of the view scope to the target location.

37. A method as in claim 35, wherein introducing comprises withdrawing the viewing scope from the sheath and advancing the plug element through the first lumen of the sheath.

38. A method as in claim 35, wherein introducing comprises advancing the plug through a second lumen of the sheath while the viewing scope remains in place in the first lumen of the sheath.

39. A method as in claim 34, further comprising locking the sheath to the viewing scope prior to introducing the assembly to the lung passageway.

40. A method as in claim 34, wherein introducing the viewing scope comprises advancing the viewing scope until a distal end of the viewing scope engages a stop element at the distal end of the sheath wherein the stop element prevents further distal advancement of the viewing scope.

41. A method as in claim 34, further comprising measuring pressure in the lung passageway using a transducer disposed on the sheath near the distal end of the sheath.

42. A method as in claim 34, wherein the sheath includes at least third and fourth inflatable cuffs spaced-apart from the first and second cuffs and wherein the method further comprises selectively inflating at least one of the third and fourth cuffs to isolate the one lung.

43. A sheath for use in combination with a viewing scope, said sheath comprising:

a flexible tubular body having a proximal end, a distal end, and a first lumen therethrough;

a sleeve slidably mounted over the flexible tubular body;

a first inflatable cuff at the distal end of the flexible tubular body; and a second inflatable cuff disposed on the sleeve and spaced apart axially for the first inflatable cuff;

wherein the flexible tubular body has a length in the range from 40 cm to 70 cm, an inside lumen diameter in the range from 1.5 mm to 10 mm, and a wall thickness in the range from 0.3 mm to 0.7 mm.

44. A sheath as in claim 43, further comprising a stop element disposed near the distal end of the tubular body to axially limit the travel of the viewing scope in the lumen.

45. A sheath as in claim 44, wherein the stop element comprises a barrier which mechanically engages a portion of the viewing scope to prevent further travel by the viewing scope in the distal direction.

46. A sheath as in claim 43, wherein a distal end of the cuff is disposed on the tubular body at a distance from the distal end of the tubular body in the range from 0 to 2 cm.

47. A sheath as in claim 43, wherein a distal end of the cuff is disposed on the tubular body at a distance from the distal end of the tubular body in the range from 0 to 2 cm.

48. A sheath as in claim 43, wherein the cuff is elastic and conforms closely to an exterior surface of the tubular body when not inflated.

49. A sheath as in claim 43, wherein the cuff has a peripheral geometry selected from the group consisting of spherical, cylindrical, disc-like, and double disc-like.

50. A sheath as in claim 43, wherein the cuff has a length in the range from 5 mm to 3 cm.

51. A sheath as in claim 43, wherein the cuff is formed as an eversion at the distal end of the tubular body.

52. A sheath as in claim 43, wherein the lumen of the flexible tubular body is coated with a lubricous coating.

53. A sheath as in claim 43, wherein the lumen of the flexible tubular body is textured to reduced friction.

54. A sheath as in claim 53, wherein the lumen is textured with protrusions.

55. A sheath as in claim 43, further comprising a proximal fitting which can be selectively sealed over the viewing scope when the viewing scope is present in the lumen of the tubular body.

56. A sheath as in claim 43, wherein the inflatable cuff is connected to an inflation lumen formed within the flexible tubular body to permit inflation thereof.

57. A sheath as in claim 43, wherein the inflatable cuff is connected to an inflation tube which is disposed externally to the flexible tubular body to permit inflation of the cuff.

58. A sheath as in claim 43, further comprising means on the flexible tubular body for measuring pressure near the distal end of the flexible tubular body.

59. A sheath as in claim 58, wherein the means comprises a pressure transducer disposed at the distal end of the tubular body.

60. A sheath as in claim 43, further comprising at least a third and a fourth inflatable cuff, wherein said second, third, and fourth inflatable cuffs are disposed directly on the flexible tubular body.

* * * * *